United States Patent [19]
Wakamoto et al.

[11] Patent Number: 5,849,252
[45] Date of Patent: Dec. 15, 1998

[54] CHARGED PARTICLE ACCELERATOR APPARATUS AND ELECTRONIC STERILIZER APPARATUS USING THE SAME

[75] Inventors: Ikuo Wakamoto; Masashi Ooya; Ichiro Yamashita; Susumu Urano, all of Hiroshima; Yuichiro Kamino; Naoki Hisanaga, both of Nagoya, all of Japan

[73] Assignee: Mitsubishi Jukogyo Kabushiki Kaisha, Tokyo, Japan

[21] Appl. No.: 611,193

[22] Filed: Mar. 5, 1996

[30] Foreign Application Priority Data

Mar. 6, 1995 [JP] Japan .................................. 7-045396
Mar. 31, 1995 [JP] Japan .................................. 7-075631

[51] Int. Cl.$^6$ ............................ H01J 31/00; H01J 23/12; H01J 25/00; H01J 29/00
[52] U.S. Cl. ............................... 422/186.04; 422/186.29; 315/500; 315/506; 315/507
[58] Field of Search ........................... 315/500, 506, 315/507; 422/186.04, 186.29

[56] References Cited

U.S. PATENT DOCUMENTS

| | | | |
|---|---|---|---|
| 3,449,618 | 6/1969 | Gallagher | 315/5.41 |
| 3,617,739 | 11/1971 | Liebl | 250/49.5 P |
| 4,093,419 | 6/1978 | Tauber et al. | 21/102 R |
| 4,146,817 | 3/1979 | McEuen et al. | 315/5.41 |
| 5,014,014 | 5/1991 | Swenson | 328/233 |
| 5,280,252 | 1/1994 | Inoue et al. | 328/233 |
| 5,483,122 | 1/1996 | Derbenev et al. | 315/5.14 |
| 5,486,703 | 1/1996 | Lovin et al. | 250/492.3 |
| 5,515,259 | 5/1996 | Stephenson | 363/59 |
| 5,532,210 | 7/1996 | Shen | 505/200 |
| 5,604,352 | 2/1997 | Schuetz | 250/492.3 |

FOREIGN PATENT DOCUMENTS

| | | |
|---|---|---|
| 0 345 006 | 12/1989 | European Pat. Off. . |
| 2 384 418 | 10/1978 | France . |
| 3812660 | 11/1989 | Germany . |
| 56091367 | 7/1981 | Japan . |
| 1169390 | 7/1989 | Japan . |
| 2094297 | 4/1990 | Japan . |

OTHER PUBLICATIONS

Database WPI, Section Ch, Week 9502, Derwent Publications Ltd., London, GB, Class A35, AN 95–011848, XP002004843 & JPA–06 298 820 (Sumitomo Heavy Ind. Ltd) 25 Oct. 1994, Abstract.

*Primary Examiner*—Daniel J. Jenkins
*Attorney, Agent, or Firm*—Wenderoth, Lind & Ponack, L.L.P.

[57] ABSTRACT

An electron beam emitted from an electron gun enters into an accelerator 8 through a magnetic lens and is accelerated by a large number of accelerating tube discs within the accelerator, resonance cavities formed thereby and a magnetic field supplied from the outside. Then, it is focused by a focusing magnet and enters into an energy analyzer and scanned by a beam scanner, and is irradiated as a beam onto a sterilization goods item. On the outside of the accelerator there is disposed a cooling jacket for making uniform the thermal expansions of the resonance cavities due to thermal load. Also, by providing frequency adjusting means for adjusting the frequency of an accelerating microwave input through an input coupler and also by the cooling jacket having its thickness gradually increased from the inlet toward the outlet so as to make the thermal expansions of the resonance cavities zero, it becomes possible to make the amount of variation in the acceleration phase zero to thereby enable provision of an accelerator apparatus with large output and high energy density. Furthermore, in the energy analyzer, a particle energy necessary for sterilization is selected by bending magnet energy means and slit and irradiated, with the result that an effective electronic sterilizer apparatus can be realized.

6 Claims, 11 Drawing Sheets

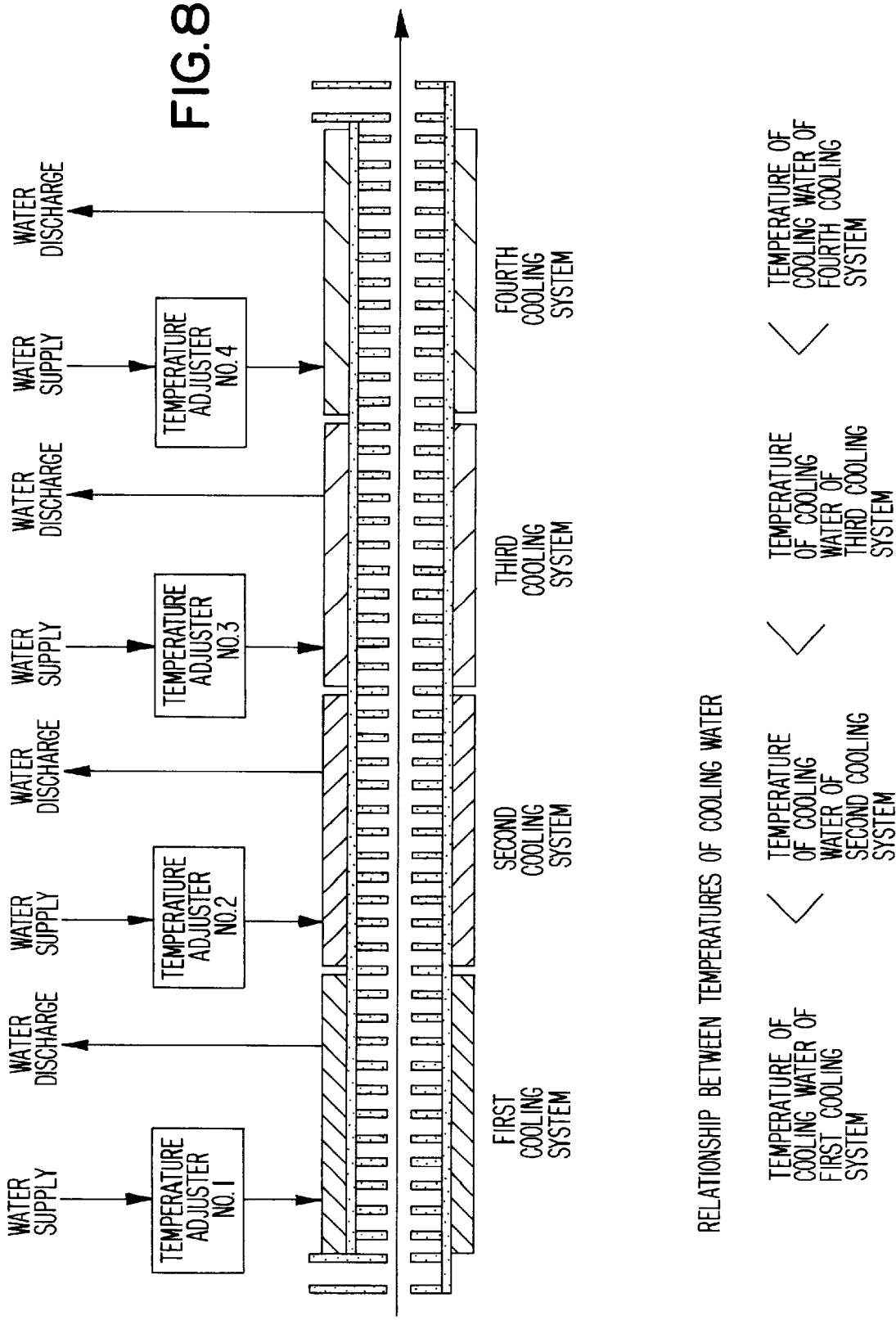

CHARGED PARTICLE ACCELERATOR APPARATUS AND ELECTRONIC STERILIZER APPARATUS USING THE SAME

BACKGROUND OF THE INVENTION

The present invention relates to a charged particle accelerator apparatus and to an electronic sterilizer apparatus designed to select a prescribed energy width of particles from the charged particles accelerated therein and irradiate them onto an object to be sterilized to thereby perform sterilization thereof.

A linear accelerator (LINAC) is composed of a large number of resonance cavities (acceleration structure) each having a very high value of Q (usually 10000 or more) regardless of whether it is a traveling wave type or standing wave type.

Acceleration of charged particles is performed by inputting a large power of resonance frequency microwaves (usually 2856 MHz or 2998 MHz) to the interior of the acceleration structure and causing generation of an acceleration electric field having a phase velocity substantially equal to that of accelerated particles. In each resonance cavity, ohm loss of the input microwave occurs within a skin depth of metallic surface and becomes thermal load of each resonance cavity (which is called "wall loss").

In a state where charged particle beam exists, supply of energy from the accelerating microwave to charged particles (beam loading) occurs. Therefore, the intensity of the microwave in each cavity is not fixed and a distribution thereof occurs.

To explain a traveling wave type electron accelerator as an example, it is usually designed into a fixed gradient type for the purpose of, for example, improving the energy conversion efficiency. Therefore, in a state where no electron beam exists, the intensity of the microwave in each cavity is approximately uniform. However, the flow of the microwave energy is as illustrated in FIG. 10 and, as illustrated in FIG. 10, a distribution occurs in the intensity of the accelerating microwave. And in proportion thereto a distribution occurs also in the wall loss to become thermal load of each cavity.

While in a conventional accelerator uniform liquid cooling was performed with respect to each cavity by use of a refrigerant having a fixed temperature, when the accelerator is used with a large output, each cavity is expanded although slightly by large thermal load, with the result that because of the Q value of each cavity being large the resonance frequency decreases. As a result, it sometimes happens that the acceleration phase is shifted with the result that the acceleration performance largely decreases.

To cope with this, there is an example adapted to make control of the temperature of the refrigerant so as to lower it as the accelerator output increases (U.S. MIT 400 MeV LINAC, reference literature: Linear Accelerators P445 to P446 P. M. Lapostolle and A. L. Septier North-Holland Publishing Company). However, in a case where an again larger output is needed, thermal expansion differs for each cavity due to the above-mentioned thermal load distribution, whereby a distribution of resonance frequency occurs with the result that the shift of the acceleration phase cannot be suppressed to within a permissible range of degree. Resultantly, there were cases where the acceleration performance decreased.

Also, in FIG. 11 there is illustrated the outline of an energy analyzer for analyzing and selecting the energy of a charged particle accelerated by the above-mentioned charged particle accelerator apparatus.

Note that explanation here will be given with electron beam being taken as an example of a particle beam. A cathode 21 generates a thermion not illustrated by being heated by a heating power source 22. The thermion is drawn out by an electric field generated between an anode 24 and the cathode 21, the anode 24 having positive potential as comparead with the cathode 21, by an acceleration power source 23, whereby an electron beam 25 is obtained. Note that the cathode 21 and anode 24 are installed within an electron gun room 26 whose interior is kept vacuumized by an evacuation means 27.

The generated electron beam 25 comes to have an energy width with respect to prescribed energy due to ripples of the acceleration power source 23, velocity distribution of thermion not illustrated generated from the cathode 21, etc. For this reason, when using the electron beam 25 in a scientific experiment or the like requiring the use of an energy width as narrow as possible, it becomes necessary to remove the electrons of outside a prescribed range of energy from the electron beam 25. To this end, generally, energy analysis is performed based on the use of the fact that the trajectory of the electron beam 25 within an electromagnetic field depends on the energy thereof.

The drawn out electron beam 25 enters into an energy analyzer installed at a succeeding stage to the electron gun room 26. As illustrated in FIG. 12 (sectional view taken along the G—G), this energy analyzer is composed of deflection magnets 28 generating a uniform magnetic field for deflecting the trajectory of the electron beam 35 in correspondence with the Larmor radius corresponding to the energy thereof, a vacuum chamber 29 installed between magnetic poles of the deflection magnets 28 and constituting a path of the electron beam 25, and a slit 30 for stopping travel of and absorbing the electron beam 25 having an energy of outside a prescribed range of energy by utilizing the difference between the Larmor radius. The thickness of the slit 30 needs to be made larger than the range of the electron beam 25. Note that the vacuum chamber 29 has its interior kept vacuumized by means of an evacuation means not illustrated.

Within a uniform magnetic field, the Larmor radius of the electron beam 25 is proportionate to the square root of the energy thereof. Therefore, when the electron beam 25 composed of electrons having various widths of energy has entered into the energy analyzer, as illustrated within a region where uniform magnetic field generates the electron beam 25 has different trajectories such as a high-energy beam 35 and a low-energy beam 36 in correspondence with the energy of each electron. As a result of this, an electron beam 31 having given energy (including the width) can be obtained through the slit 30 by suitably setting the position and width of an opening of the slit 30.

The thus-generated electron beam 31 having its energy width narrowed is used for various scientific experiments by being caused to enter into, for example, an examination room 32 whose interior is kept vacuumized by an evacuation means not illustrated and then being made incident upon a target 33 and then detected by a detector 34.

Note that since as mentioned above the slit 30 directly stops and absorbs the electrons of outside a prescribed range of energy, it absorbs an amount of heat which corresponds to (the energy of the electron incident upon the slit 30×the amount of current). For this reason, in order to eliminate this thermal load, it is necessary to cool the slit 30.

In the deflection magnets 28 used for performing the energy analysis, the intensity of the magnetic field generating between the magnetic poles thereof is inversely proportional to a spacing 37 between the magnetic poles. For this reason, when constructing the energy-analyzing deflection magnets 28, it is preferable to make the spacing 37 between the magnetic poles as narrow as possible so that the cost involved may become as low as possible (by using a low capacitance power source, minimizing the number of turns of the coils wound around the deflection magnets, and making the power consumption low). Accordingly, the width t of the slit 30 is narrower than the spacing 37 between the magnetic poles, further even the internal width W of the vacuum vessel 29 installed therebetween. On the other hand, it is necessary that part of the slit 30 has an opening 38 for permitting passage therethrough of the electron beam 31 corresponding to a desired width of energy.

OBJECT AND SUMMARY OF THE INVENTION

In the conventional accelerator, when using it with a large output as mentioned above, each cavity is expanded due to large thermal load, whereby it sometimes happened that the resonance frequency thereof was lowered and the acceleration phase was shifted, with the result that the acceleration performance largely decreased.

Also, in the energy analyzer designed to select and extract prescribed particles from the charged particles accelerated by the above-mentioned accelerator, in order to remove the thermal load imparted to the slit portion, it is necessary to cause flow of a coolant from outside the vacuum vessel illustrated in FIG. 11 to this slit portion. However, as mentioned previously, setting of the slit width t is limited by the internal width W of the vacuum vessel 29 and also by the required diameter of the opening of the open portion. Therefore, regarding a piping for causing flow of a coolant, one having a large inside diameter cannot be used. As a result, it becomes difficult to ensure a required flow of cooling for removing the thermal load and, in addition, the pressure loss becomes large. Particularly, when using a large output of beam, there was the inconvenience that this tendency became prominent.

Further, while cooling of the slit 30 needs to be done at a position of interference thereof with beam, when stopping and absorbing a beam having a wide range of energy by means of the same slit, it is necessary to lengthen the length of the slit. In this case, since there arises the necessity of forming many flow passages with respect to the interior of the slit 30, there was the inconvenience that the number of steps for processing the slit portion increased and, in addition, the pressure loss became larger than that in the above-mentioned case.

The present invention has been made in order to solve the above-mentioned problems and an object of the present invention is to realize a large output of charged particle accelerator apparatus by minimizing the amount of shift of the acceleration phase in each cavity thereof under high thermal load.

Another object of the present invention is to provide an energy analyzer designed to input and analyze the particles accelerated by this charged particle accelerator apparatus to thereby enable selection of prescribed particles alone with the pressure loss being kept decreased.

Still another object of the present invention is to provide an electronic sterilizer apparatus prepared by combining the charged particle accelerator apparatus and the energy analyzer and designed to accelerate an electron beam, select a necessary particle beam therefrom, and irradiate it over a goods item and thereby perform sterilization with respect thereto.

To attain the above objects, the present invention provides the following means.

(1) According to a first aspect of the present invention, there is provided a charged particle accelerator apparatus comprising an accelerating tube having a plurality of resonance cavities formed axially in its interior and having charged particles caused to pass therethrough from one end side thereof to the other end side thereof, an input coupler provided at one end portion of the accelerating tube for inputting an accelerating microwave, and a dummy load provided at the other end portion thereof through an output coupler, the charged particle accelerator apparatus being characterized by further comprising cooling means provided on the outside of the accelerating tube for making uniform thermal expansions of the respective resonance cavities with respect to a thermal load distribution decreasing from the one end side of the accelerating tube toward the other end side thereof and frequency adjusting means for adjusting the frequency of the accelerating microwave input through the input coupler to a resonance frequency of the respective resonance cavities having been subjected to uniform thermal expansion.

(2) According to a second aspect of the present invention, there is provided a charged particle accelerator apparatus comprising an accelerating tube having a plurality of resonance cavities formed axially in its interior and having charged particles caused to pass therethrough from one end side thereof to the other end side thereof, an input coupler provided at one end portion of the accelerating tube for inputting an accelerating microwave, and a dummy load provided at the other end portion thereof through an output coupler, the charged particle accelerator apparatus being characterized by further comprising cooling means provided on the outside of the accelerating tube for making uniform thermal expansions of the respective resonance cavities with respect to a thermal load distribution decreasing from the one end side of the accelerating tube toward the other end side thereof.

(3) According to a third aspect of the present invention, there is provided an electronic sterilizer apparatus comprising an electron gun for generating a charged particle beam, the charged particle accelerator apparatus under the above item (1) or (2) for accelerating the charged particle beam, an energy analyzer for taking out only a beam component having a prescribed width of energy from the accelerated charged particle beam, and a scan horn for irradiating the charged particle beam from the energy analyzer onto a sterilization object while scanning it thereover.

(4) According to a fourth aspect of the present invention, there is provided an electronic sterilizer apparatus as set forth under the above item (3), the electronic sterilizer apparatus being characterized by comprising the energy analyzer which is an analyzer adapted to cause the charged particle beam from the charged particle accelerator apparatus to enter into a vacuum chamber and cause deflection of this beam by use of a magnetic field to thereby analyze the energy thereof, the analyzer comprising a low-energy beam absorption chamber disposed at such a position as to surround a center of the radius of curvature of a trajectory of the deflected beam within the vacuum chamber constituting a path of this beam and as to stop forward travel of a low-energy beam contained therein, the low-energy beam absorption chamber being arranged to be cooled, a high-energy beam absorption chamber disposed at such a position as to oppose the center of the radius of curvature of the trajectory within the vacuum chamber and as to stop forward travel of a high-energy beam contained in the beam, the high-energy beam absorption chamber being arranged to be cooled, and a movable type slit whose opening width is adjusted on the trajectory of the deflected beam to thereby enable selection of an analyzable range of energy thereof, the movable type slit being arranged to be cooled.

(5) According to a fifth aspect of the present invention, there is provided an electronic sterilizer apparatus as set forth under the above item (4), the electronic sterilizer apparatus being characterized by comprising the energy analyzer wherein the movable type slit is provided with a plurality of slits each of which can be independently driven and positionally set.

In the inventions under the above items (1) and (2), the cooling means disposed on the outside of the accelerating tube has high cooling performance at one end side thereof and the cooling performance thereof decreases toward the other end side thereof. Therefore, the thermal expansions of the respective resonance cavities can be made uniform with respect to the thermal load gradually decreasing from one end side toward the other end side, thereby enabling making-uniform of the shifts of the resonance frequencies.

Also, since the accelerating microwave input through the input coupler has its frequency adjustable by the frequency adjusting means, the frequency thereof can be made to coincide with the resonance frequency of the resonance cavity which has been varied due to the thermal expansion.

For this reason, it is possible to make the amount of variation in the acceleration phase zero by cooling the respective resonance cavities by the cooling means and adjusting the accelerating microwave by the frequency adjusting means. This makes it possible to realize an accelerator apparatus with large output and high energy density.

Also, under the above item (2), since the cooling means performs cooling so as to make the thermal expansion of each resonance cavity zero, it is possible to realize a large output and high energy accelerator without using the frequency adjusting means.

In the inventions under the above items (3) and (4), when having entered into the vacuum chamber, the generated particle beam undergoes deflection by a magnetic field and travels while the trajectory thereof is describing the Larmor radius in correspondence with the energy thereof. Of this deflected particle beam, the low-energy particle beam is caught by and absorbed into the low-energy beam absorption chamber disposed along the trajectory of the particles about the center of the radius of curvature thereof and so as to stop midway the travel of this low-energy particle beam. The low-energy particle beam absorption chamber is cooled by cooling water or the like, whereby a rise in the degree of heat thereof is suppressed. Of the deflected particle beam, the high-energy particle beam is deflected more largely than the low-energy particle beam. Therefore, it is caught by and absorbed into the high-energy beam absorption chamber disposed in such a manner as to oppose it and this high-energy beam absorption chamber is also similarly cooled by passage of cooling water therethrough. The particle beam having its energy width narrowed without being caught by and absorbed into the low-energy and high-energy beam absorption chambers reaches the movable slit, whereby part thereof is again caught by and absorbed into a peripheral portion of the slit. Thus, only a particle beam having a prescribed center energy width passes through the opening portion of the slit and is irradiated onto a sterilization object through the scan horn.

Further, in the invention under the above item (5), a plurality of slits are provided and each of these slits is independently driven and adjusted. Therefore, when selection of energy width is made according to the necessity, for example each slit can be independently adjusted by being provided as a high-energy side slit or a low-energy side slit. Thus, selection of energy width can be made over a wide range of energy.

In the charged particle accelerator apparatus according to the present invention, there is provided on the outside of the accelerating tube the cooling means for making uniform the thermal expansions due to thermal load of the plurality of resonance cavities disposed axially within the accelerating tube and there is provided the frequency adjusting means for adjusting the frequency of the accelerating microwave input through the input coupler. Also, there is provided on the outside of the accelerating tube the cooling means for making the thermal expansions of the resonance cavities zero. As a result, it becomes possible to make the amount of variation in the acceleration phase zero, which makes it possible to realize an accelerator apparatus with large output and high energy density.

By combining the electron gun, the above-mentioned charged particle accelerator apparatus and an energy analyzer, the electronic sterilizer apparatus according to the present invention enables selection of a prescribed charged particle beam and irradiation thereof onto a goods item to be sterilized and enables easy sterilization thereof. Also, the energy analyzer is applied to the electronic sterilizer apparatus by being provided with the low-energy beam absorption chamber for stopping travel of a low-energy particle beam about a center of the radius of curvature of the trajectory of the charged particle beam caused to enter from the above-mentioned charged particle accelerator apparatus into the vacuum chamber and deflected by a magnetic field within this vacuum chamber, the low-energy beam absorption chamber being cooled, the high-energy beam absorption chamber for stopping travel of a high-energy particle beam at a side opposing this center of the radius of curvature of the trajectory, the high-energy beam absorption chamber being cooled, and the movable slit for selecting an analyzable range of energy, the movable slit being cooled and the movable slit having a plurality of slits which can be independently driven. Therefore, the following advantages can be obtained.

(1) Since there are provided the low and high energy beam absorption chambers and low and high energy particles other than the object center energy width particles are removed from the particle beam and these absorption chambers are cooled whereupon the resulting particle beam is caused to pass through the slit portion, the entire thermal load becomes effectively removed with the result that the pressure loss of coolant in the energy analyzer can be decreased as much as possible. Thus, necessary specification for supplementary equipment to the electronic sterilizer apparatus can be reduced.

(2) Since the slit is made into a movable type and, as under the above item (1), the cooling effect has been improved, the energy analyzer enabling energy analysis over a wide range of energy can be produced at a low cost to thereby enable realization of an inexpensive electronic sterilizer apparatus. And (3) Further, since the slit is provided with a plurality of movable slits, it can be used as a high-energy slit or a low-energy slit, with the result that the energy analyzer enabling arbitrary selection of energy width over a wide range of energy can be realized and applied to the electronic sterilizer apparatus.

BRIEF DESCRIPTION OF THE DRAWINGS

FIG. 8 illustrates a case where the cooling water jacket according to the embodiment is formed by independent cooling systems;

DETAILED DESCRIPTION OF THE PREFERRED EMBODIMENT

Figure 1:
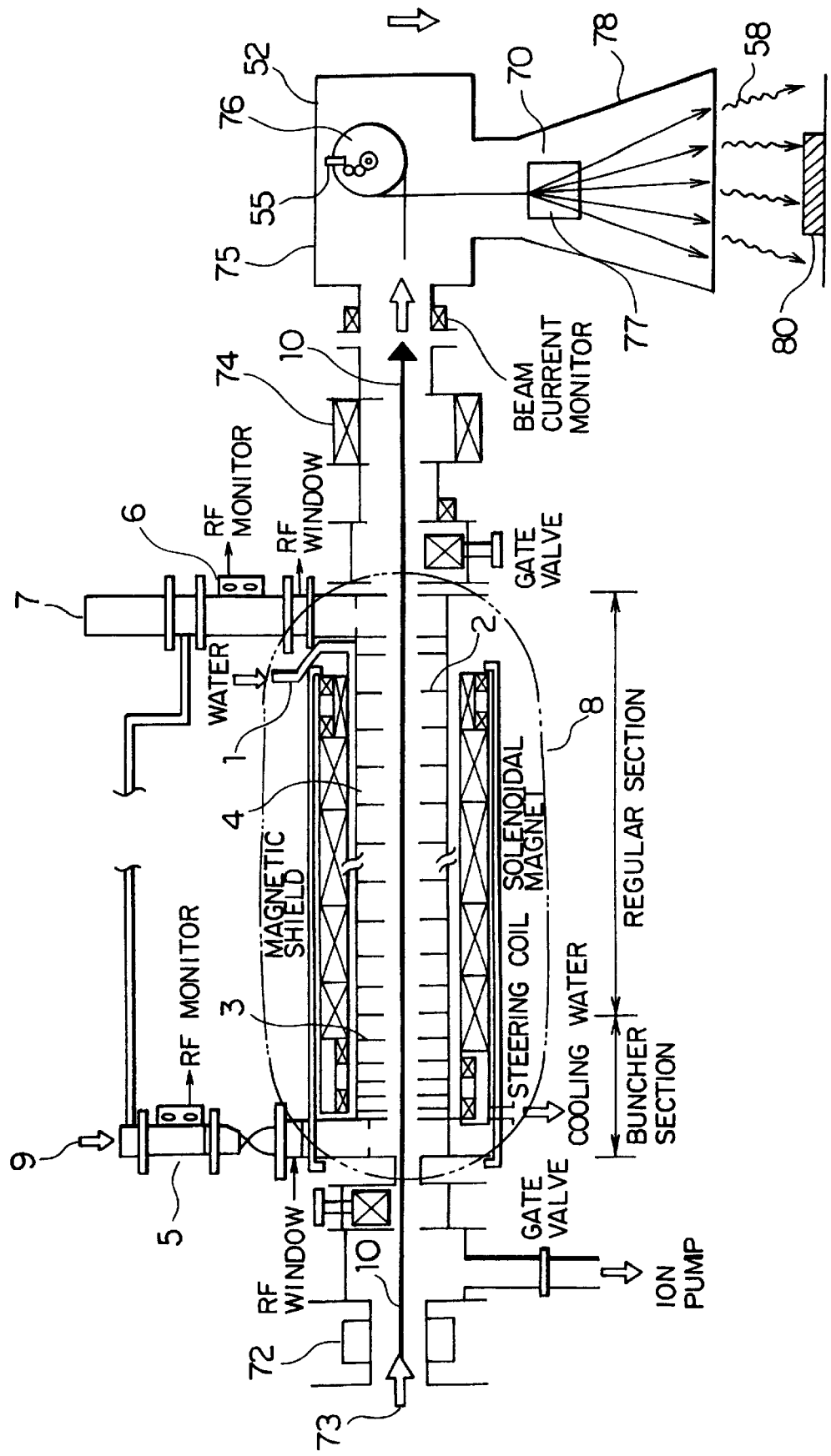
FIG. 1 is an entire structural view illustrating an electronic sterilizer apparatus provided with a charged particle accelerator apparatus, energy analyzer and scan horn according to an embodiment of the present invention.

An embodiment of the present invention will now be explained with reference to the drawings. FIG. 1 illustrates an entire structural view of an electronic sterilizer apparatus according to an embodiment of the present invention. A main part thereof is composed of a charged particle accelerator apparatus, energy analyzer and scan horn. The charged particle accelerator apparatus in FIG. 1 will be explained later in detail with reference to FIGS. 2 to 8, and the energy analyzer will be explained later in detail with reference to FIG. 9. Therefore, in this figure, only a principal portion having relevancy to the present invention will be explained with reference thereto.

In the figure, an electron beam 10 enters from an electron gun 73 into an accelerating tube 8 through a magnetic lens 72. In the accelerating tube 8, a large number of acceleration spacers 2 are provided to thereby constitute resonance cavities 4. The accelerating tube 8 accelerates the electron beam 10 while an outer periphery thereof is being cooled by a cooling water jacket 1. The electron beam 10 is focused by a focusing magnet 74 and is thereby allowed to enter into the energy analyzer 75. The energy analyzer 75 has a movable type slit 55 within a vacuum chamber 52 and also has a bending magnet energy means 76 by means of which a prescribed particle beam component is selectively allowed to pass through a slit 55 to thereby provide beams 58. The beams 58 are scanned at a prescribed angle and over a prescribed width by a beam scanner 77 having a beam scan magnet 70. That is, the beams 58 are irradiated from a scan horn 78 over a sterilization goods item, thereby performing sterilization with respect thereto.

Next, the charged particle accelerator apparatus applied to the above-explained electronic sterilizer apparatus will be explained in detail with reference to FIGS. 2 to 8. In FIG. 2, this embodiment refers to a case of a traveling wave type 25 KW beam output electron accelerator wherein an accelerating microwave having a frequency of 2856 MHz is used and the designed operation temperature is 30° C.

Figure 2A:
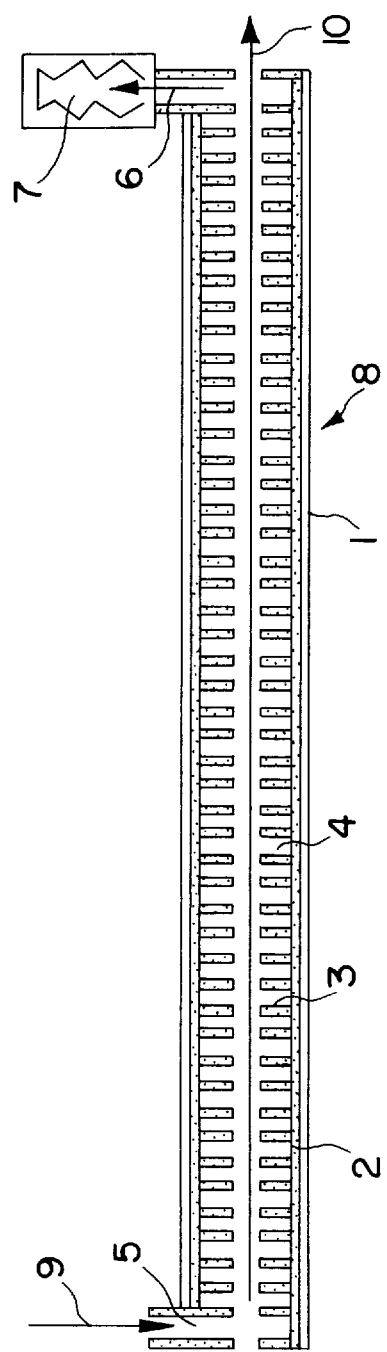
FIG. 2 illustrates a charged particle accelerator apparatus according to an embodiment of the present invention, FIG. 2(a) illustrating an entire electron accelerator and FIG. 2(b) illustrating a cooling water jacket.
Figure 2B:
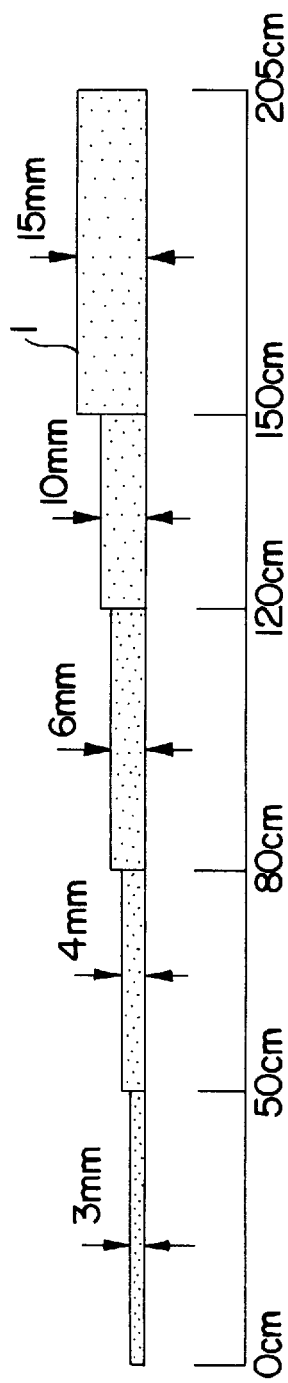

In this embodiment illustrated in FIG. 2, an electron accelerator, comprising, as illustrated in FIG. 2(a), an accelerating tube 8 provided with accelerating spacers 2 on it s internal surface and a plurality of accelerating tube discs 3 therewithin which is orthogonal to a center axis thereof, resonance cavities 4 being formed between the accelerating tube discs 3, an input coupler 5 connected to a left end side of the accelerating tube 8 for inputting an accelerating microwave 9, and a dummy load 7 connected to a right end portion of the accelerating tube 8 through an output coupler 6, is provided, on the outside of the accelerating tube 8, with a cooling water jacket 1 whose thickness is gradually increased in such a manner that, as illustrated in FIG. 2(b), the thickness thereof over an axial distance of 50 cm as measured from around the inlet at the left end of the accelerating tube 8 is as the smallest as 3 mm, the thickness thereof over an axial distance of from 50 cm to 80 cm is 4 mm, the thickness thereof over an axial distance of from 80 cm to 120 cm is 6 mm, the thickness thereof over an axial distance of from 120 cm to 150 cm is 10 mm, and the thickness thereof over an axial distance of from 150 cm to the outlet is 15 mm.

In the above arrangement, cooling of the accelerating tube 8 is performed by using pure water of 30° C. and by this pure water axially flowing through the cooling water jacket 1 provided outside the accelerating tube 8 at a flow velocity of 300 L/min. An accelerating microwave 9 is input from the input coupler 5 at the left end of the accelerating tube 8 and travels toward the right end thereof while losing its energy by the wall loss and electron acceleration, passing through the output coupler 6 to reach the dummy load 7 in which the microwave is consumed.

Figure 3:
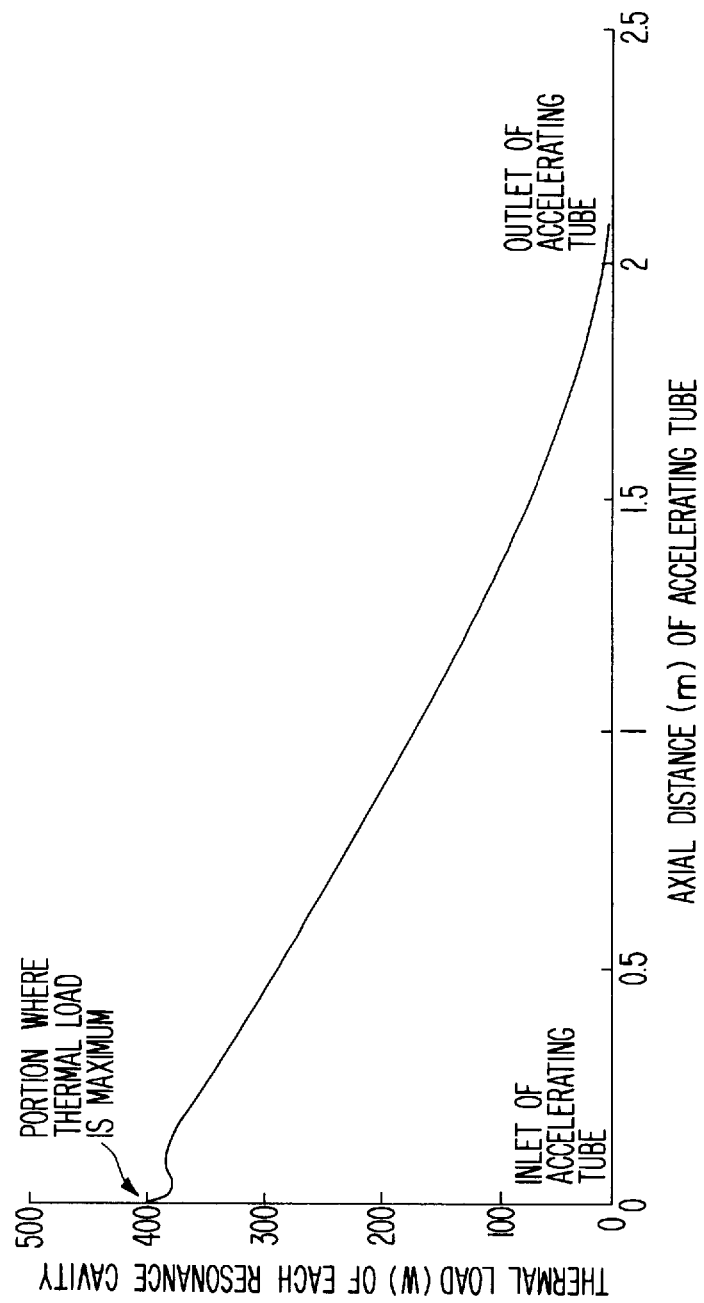
FIG. 3 illustrates a thermal load distribution of respective resonance cavities when the apparatus according to the embodiment has an output power of 25 KW.

FIG. 3 illustrates a thermal load distribution when the electron accelerator of this embodiment has a beam output of 25 KW. The thermal load becomes maximum at around the inlet of the accelerating tube 8, and thereafter, because the energy of the accelerating microwave 9 continues to be imparted to the electrons, gradually decreases and, at around the outlet of the accelerating tube 8, becomes approximately zero.

Figure 4A:
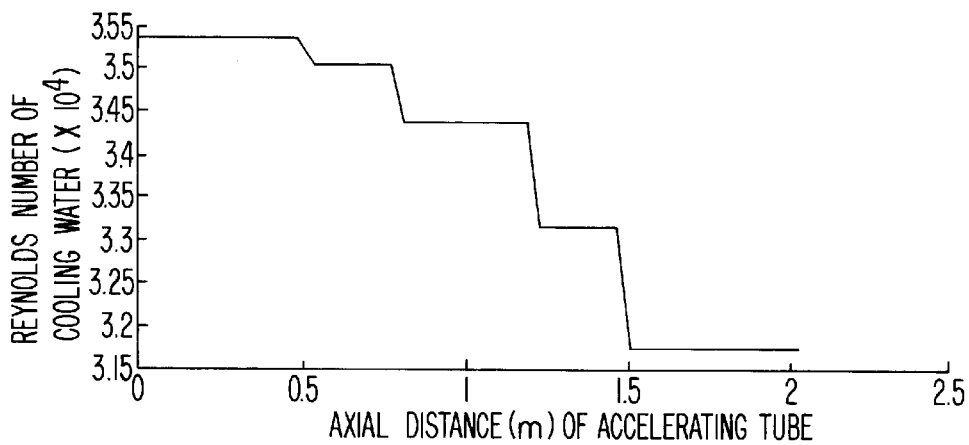
FIG. 4 illustrates the effect of the cooling water jacket according to the embodiment, FIG. 4(a) illustrating the Reynolds number of cooling water, FIG. 4(b) illustrating the frequency shift of an accelerating tube, and FIG. 4(c) illustrating the phase shift of the frequency of the accelerating microwave.
Figure 4B:
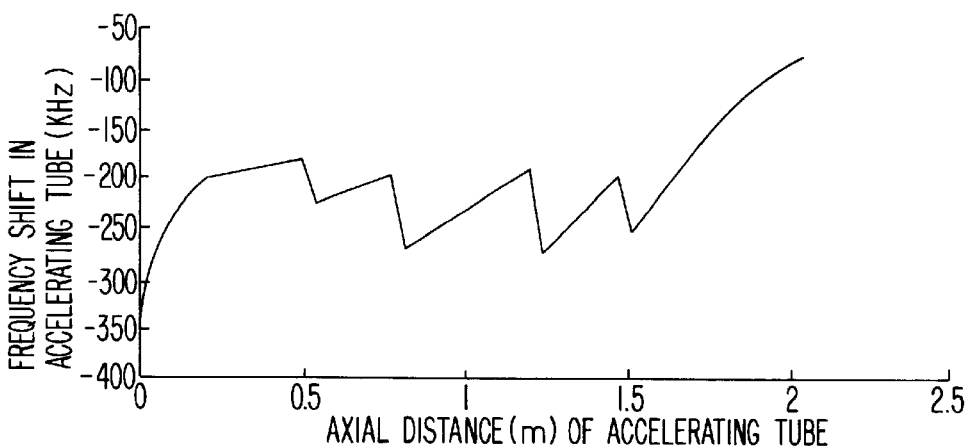

When cooling has been performed using the cooling water jacket 1, the Reynolds number of the cooling water varies as illustrated in FIG. 4(a) and the thermal conductivity from the accelerating tube 8 to the cooling water is controlled with the result that the temperature of the accelerating tube is made uniform regardless of the thermal load distribution. Whereby, the frequency shift in the accelerating tube is made substantially uniform as illustrated in FIG. 4(b).

Figure 4C:
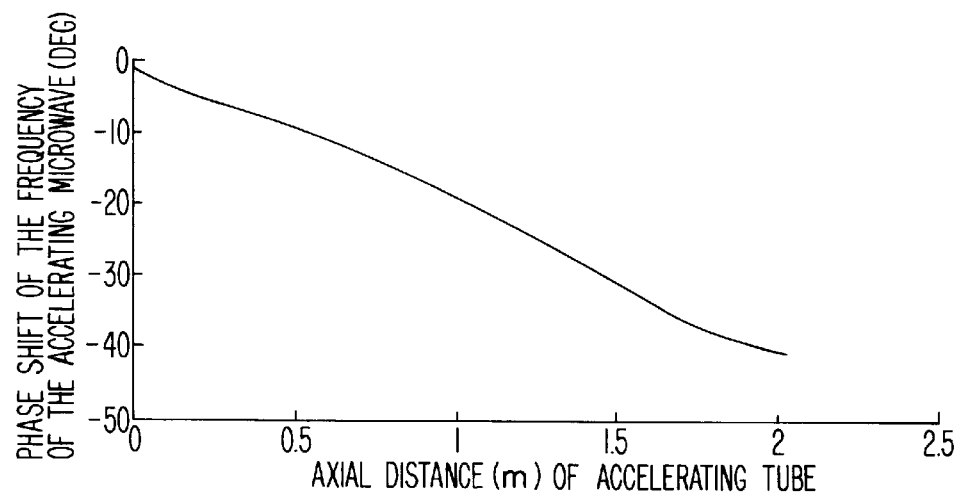

However, even when the above cooling has been performed, since the phase shift of the frequency of the accelerating microwave becomes 40° or so at around the outlet of the accelerating tube as illustrated in FIG. 4(c), the acceleration characteristic largely deteriorates. For this reason, it is necessary either to shift down the frequency of the accelerating microwave or to further decrease the temperature of the cooling water from 30° C. down to a lower temperature.

The reason why the acceleration characteristic can be thereby improved is as follows. That is, a relationship expressed by the following equation (1) exists between the amount of shift of the resonance frequency in each cavity and the amount of variation in the phase of the frequency of the accelerating microwave, whereupon if making-uniform of the shifts between the resonance frequencies have been achieved, it is possible to make zero the amount of variation in the phase of an accelerated beam by causing variation of the accelerating microwave by the extent corresponding to the amount of shift of the resonance frequency (even when the shifts between the resonance frequencies have not yet been made completely uniform, it is possible to suppress the amount of variation in the phase of the frequency of the accelerating microwave to a small value).

$$\phi(1) = \int_{x=0}^{x=1} K(x)\Delta f(x)dx \tag{1}$$

where x: the coordinate in the axial direction of the accelerating tube

φ(I): the amount of variation in the phase of the accelerated beam

I: the position in the axial direction of the accelerating tube

K(x): the value determined by the configuration of each cavity

Δf(x): the amount of shift of the resonance frequency in each cavity

Also, the above-mentioned reason why the acceleration characteristic can be improved is as follows. That is, a relationship of direct proportion exists between the shift of the resonance frequency and (temperature of the refrigerant-designed temperature of the accelerating tube), whereupon it is possible to obtain the same effect by controlling the temperature of the liquid cooling refrigerant instead of controlling the resonance frequency.

Figure 5A:
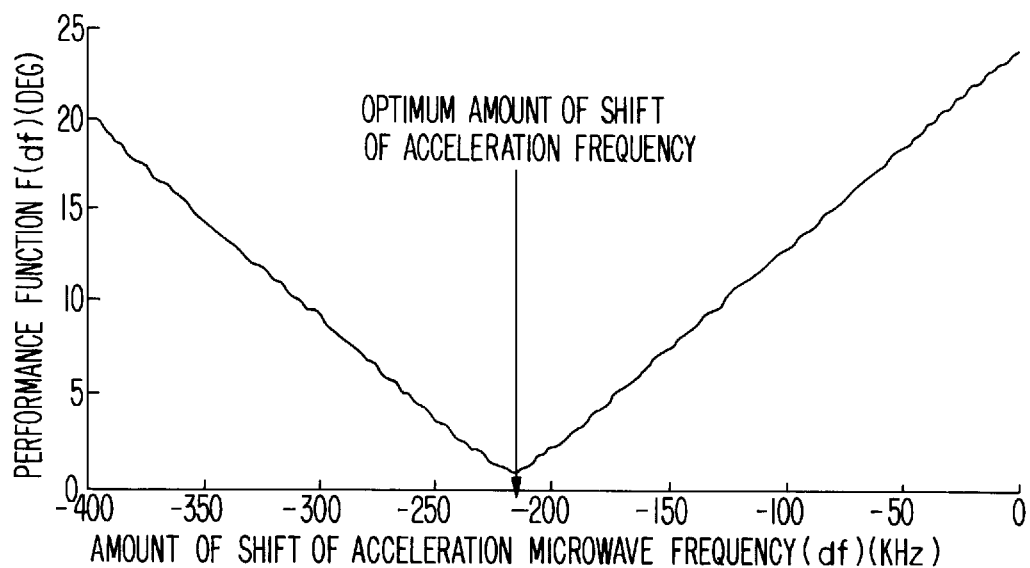
FIG. 5 illustrates the effect obtained by accelerating microwave frequency adjustment according to the embodiment, FIG. 5(a) illustrating performance function, and FIG. 5(b) illustrating the phase shift of the frequency of the accelerating microwave.

When it is desired to improve the acceleration characteristic by using a system of shifting the frequency of the accelerating microwave, an optimum amount of shifted frequency can be easily determined by obtaining the numeric value of df minimizing a performance function F(df) expressed by the following equation (2). That is, in case of this embodiment, the frequency which corresponds to a minimal point indicated in FIG. 5(a) is the numeric value of df.

$$F(df) = \sqrt{\frac{\int_{1=0}^{1=L} \phi(1)^2 d1}{L}} \tag{2}$$

where df: the required amount of shifted frequency

φ(1): the amount of variation in the acceleration phase

L: the length of the accelerating tube

Figure 5B:
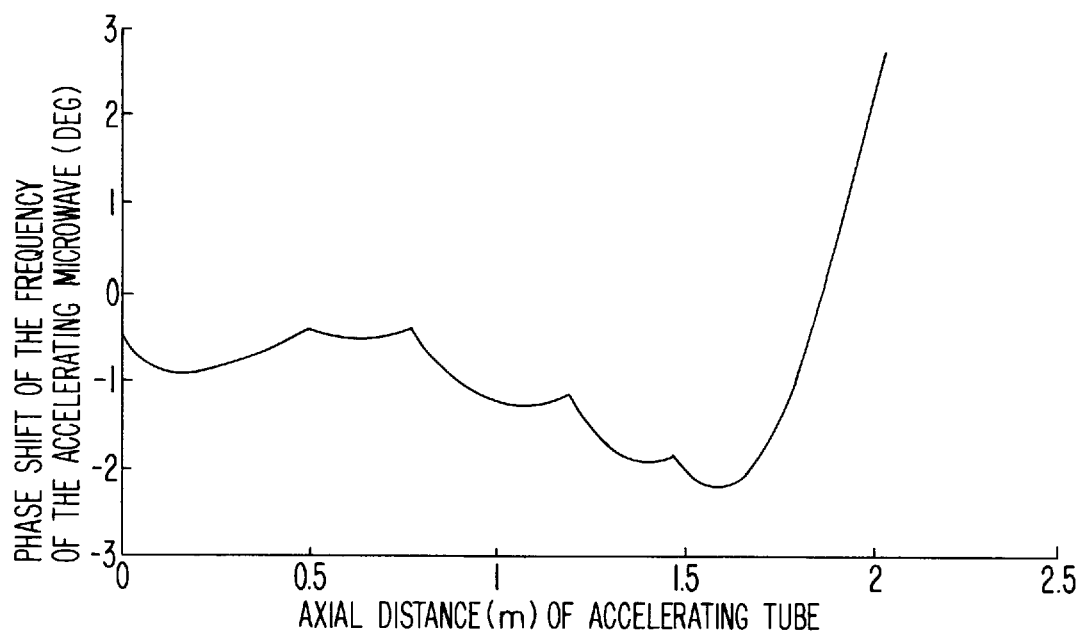

FIG. 5(b) illustrates an amount of phase shift of the accelerated microwave when the frequency of the accelerating microwave has been shifted by df. As seen from this FIG. 5(b), a low accelerated phase variation amount (±3° or less) which was impossible with the conventional cooling system and accelerating frequency controlling system is achieved. As a result, even when acceleration output is large, procurement of excellent acceleration characteristics can be expected.

While the thermal load cooling system according to this embodiment is the system of controlling the Reynolds number by the thickness of the cooling water channel as mentioned above, other various systems of cooling can be considered as follows. And any system of cooling which can exhibit the same function as in the case of this embodiment is included in the claimed scope of the present invention.

Figure 6A:
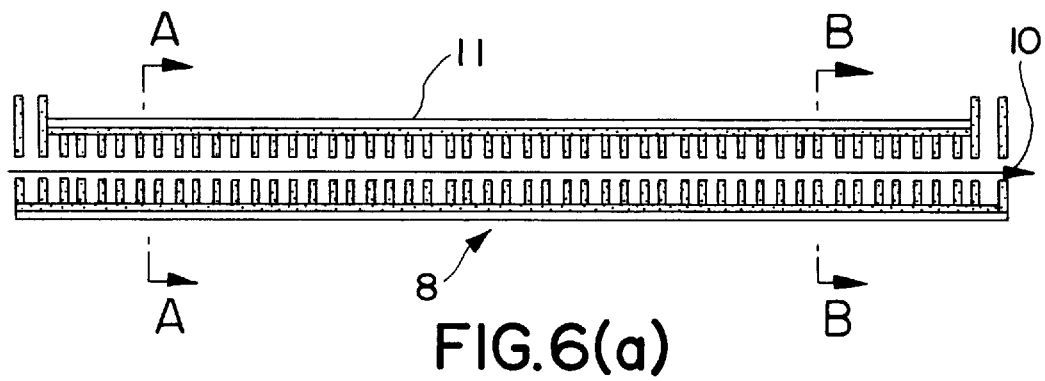
FIG. 6 presents views illustrating a case where the cooling water jacket according to the embodiment is of another system.
Figure 6B:
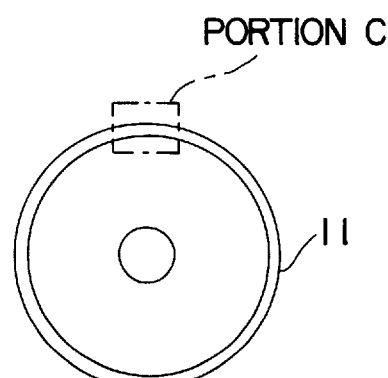
Figure 6C:
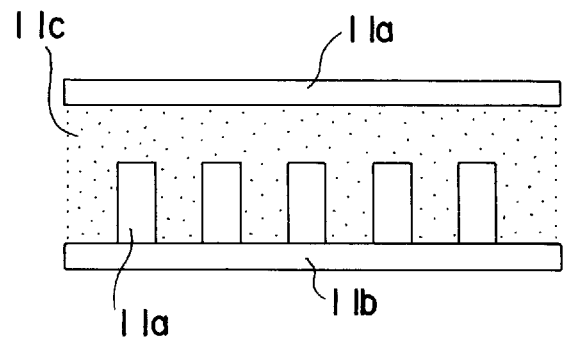
Figure 6D:
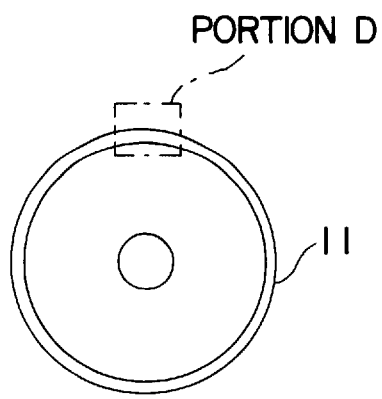
Figure 6E:
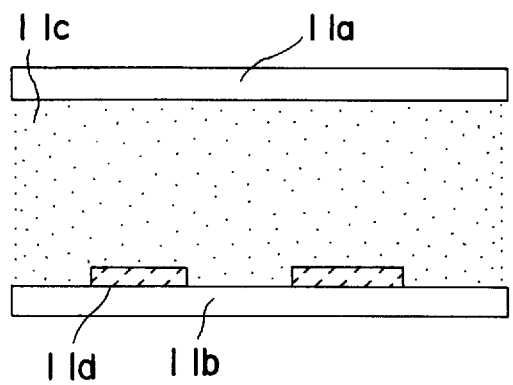
Figure 7A:
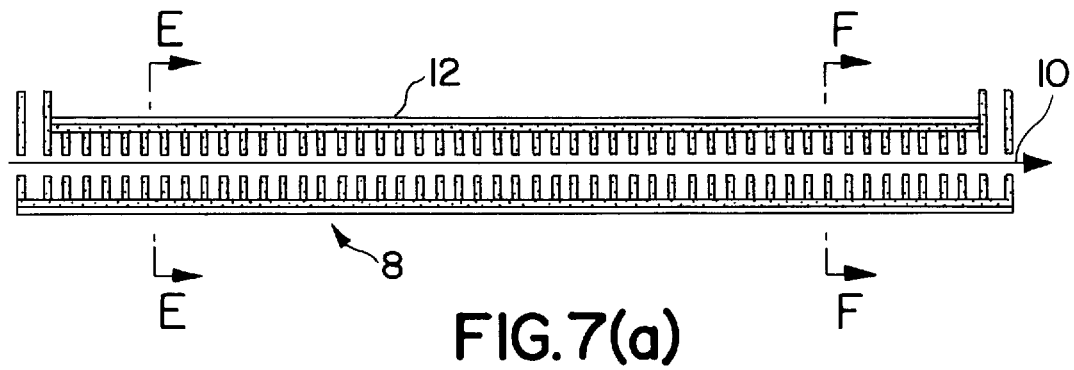
FIG. 7 presents views illustrating a case where the cooling water jacket according to the embodiment is of still another system.
Figure 7B:
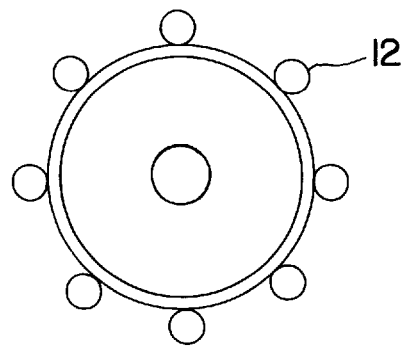
Figure 7C:
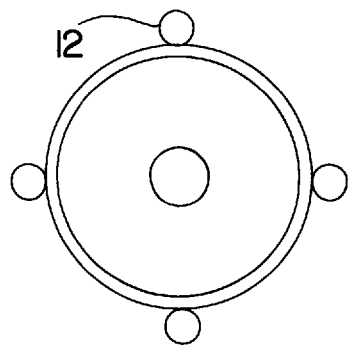
Figure 7D:
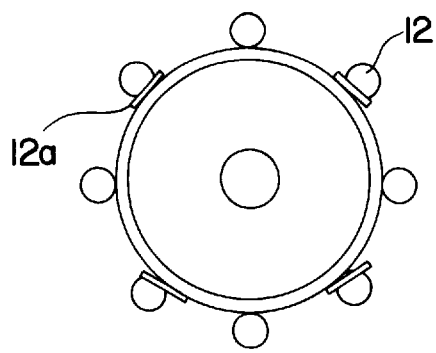

FIG. 6(a) illustrates a system of controlling the cooling performance by controlling the area of contact of cooling water jacket with the cooling water, FIG. 6(b) being a cross-sectional view taken along the line A—A of FIG. 6(a), wherein a contact surface 11a between the cooling water jacket 11 and the cooling water is shaped like teeth to thereby increase the contact area therebetween and thereby increase the cooling performance. FIG. 6(c) is a detailed sectional view of a portion (C) illustrated in FIG. 6(b), illustrating the contact surface 11a within the cooling water jacket. Also, FIG. 6(d) is a cross-sectional view taken along the line B—B of FIG. 6(a) for brevity, illustrating a system of decreasing the cooling performance by providing a structure wherein part of the contact surface is covered by materials 11d of a low thermal conductivity or alternatively the flow of the cooling water is obstructed on around the contact surface. FIG. 6(e) illustrates a state of the materials 11d. Also, FIG. 7(a) illustrates a system of increasing the cooling performance by forming the cooling water jacket with the use of pipes 12 and increasing the number thereof as illustrated in FIG. 7(b) which is a cross-sectional view taken along the E—E of FIG. 7(a) or by increasing the number of fins within the pipe and increasing the adherence area between the pipes 12 and the accelerating tube 8, and a system of decreasing the cooling performance by decreasing the number of the pipes, decreasing the adherence area of the pipes 12 to the accelerating tube 8 as illustrated in FIG. 7(c), or disposing materials 12a of a low thermal conductivity at the portions of adherence and clamping them between the pipes 12 and the accelerating tube 8 as illustrated in FIG. 7(d).

Further, FIG. 8 illustrates a type which is provided with independent cooling systems at respective portions of the accelerating tube 8, whereby the temperature of the cooling water is varied in correspondence with thermal load. In this type, the temperature of the cooling water is made the lowest at around the input coupler 5 and is increased toward the output coupler 6.

Figure 9:
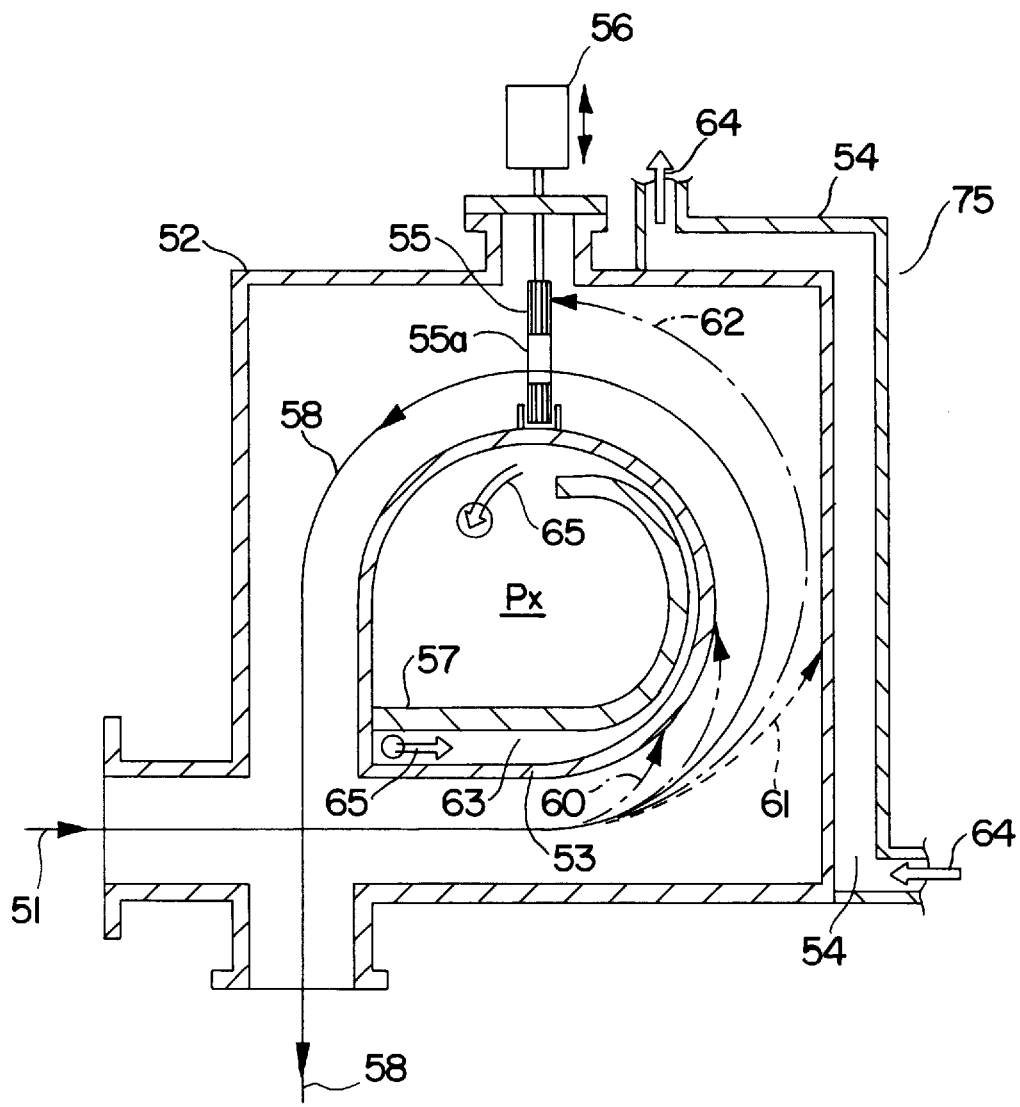
FIG. 9 is a sectional view illustrating the outline of the energy analyzer according to the embodiment of the present invention.
Figure 10A:
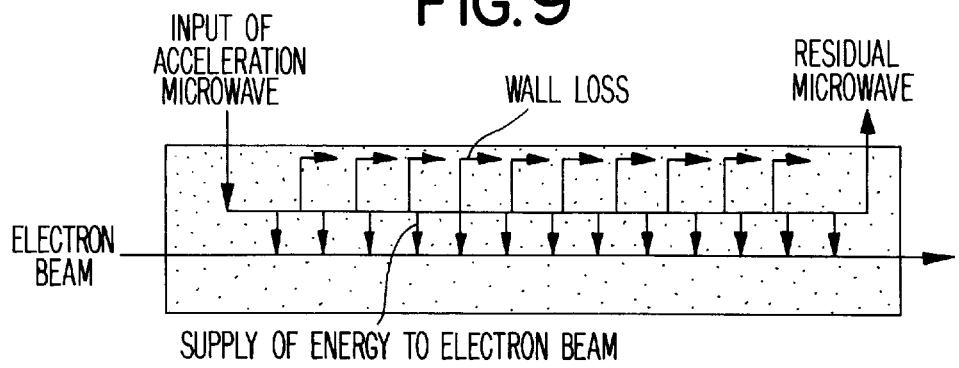
FIG. 10 illustrates a conventional charged particle accelerator apparatus.
Figure 10B:
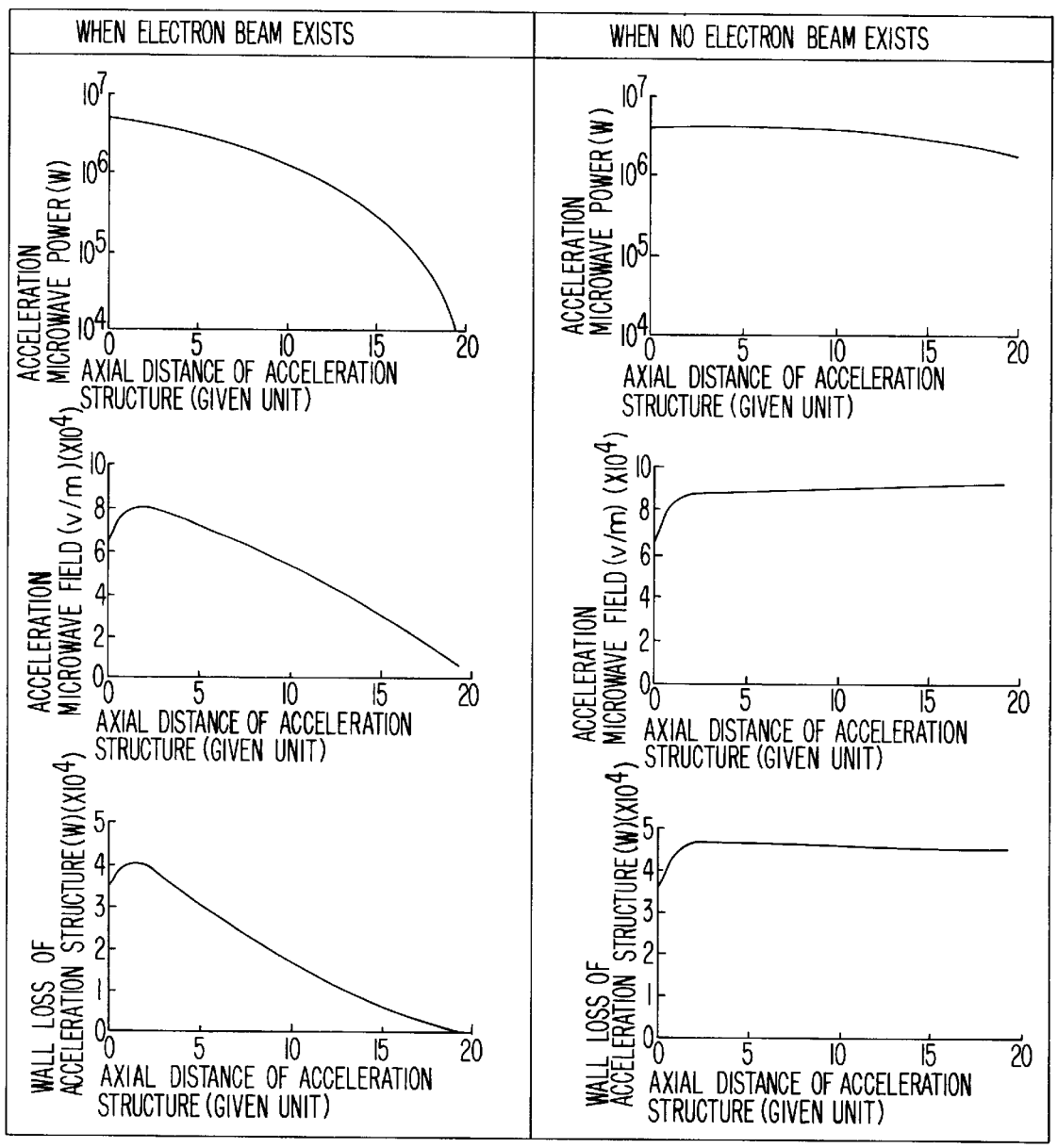
Figure 11:
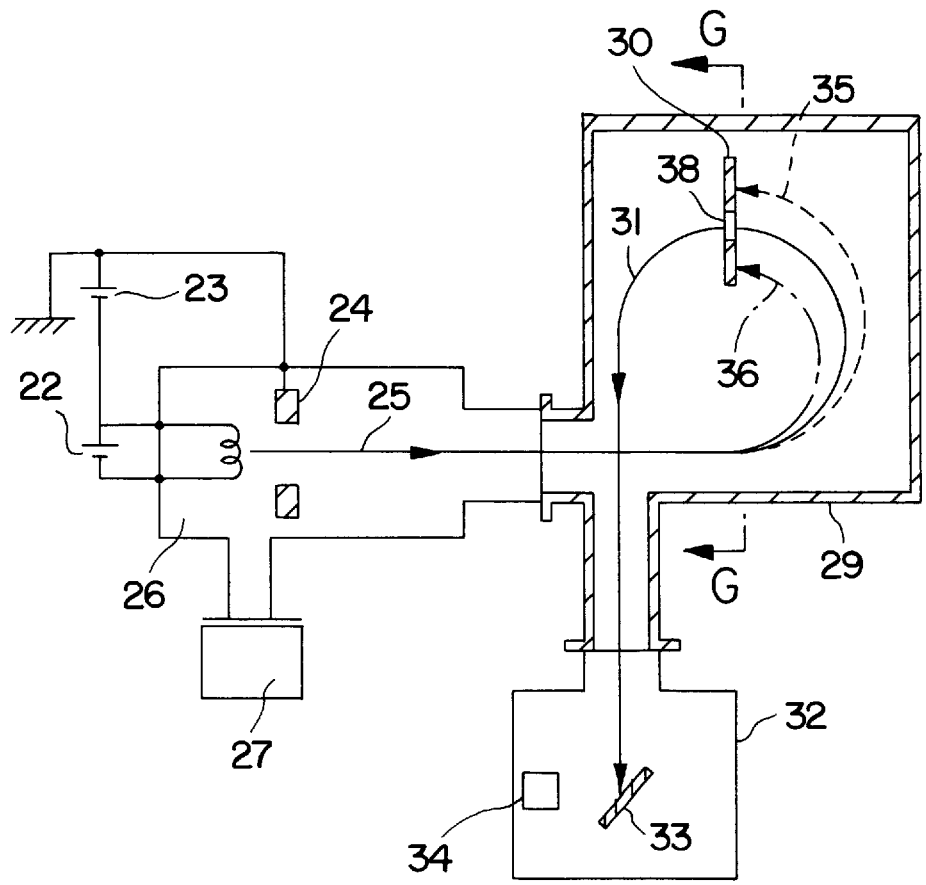
FIG. 11 illustrates the outline of a conventional energy analyzer.
Figure 12:
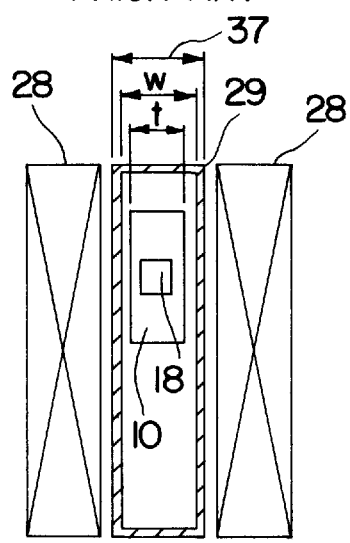
FIG. 12 is a sectional view taken along the line G—G of FIG. 11.

Next, the energy analyzer which is applied to the electronic sterilizer apparatus of FIG. 1 according to the present invention will be explained concretely with reference to FIG. 9. FIG. 9 is a sectional view illustrating this energy analyzer, wherein illustration is made with the electron beam generator section being omitted. Since the structure of the electron beam generator section is the same as that illustrated in FIG. 11, detailed explanation thereof is omitted.

An electron beam 51 which has been generated from an electron beam generator not illustrated enters into the energy analyzer. The energy analyzer comprises deflection magnets not illustrated each of which generates a uniform magnetic field for deflecting the trajectory of the electron beam 51 in correspondence with the Larmor radius corresponding to the electron beam, a vacuum chamber 52 disposed between magnetic poles of the deflection magnets and constituting a path for the electron beam 51, and a low-energy beam absorption chamber 53 disposed at a fixed position for the purpose of stopping travel of a low-energy particle beam 60 in such a manner as to surround a center P of the radius of curvature of the trajectory of the electron beam 51 when this trajectory has been deflected by the magnetic field, the low-energy beam absorption chamber 53 being cooled. It further comprises a high-energy beam absorption chamber 54 disposed at a fixed position for the purpose of stopping travel of a high-energy particle beam 61 in such a direction as to oppose the center P of the radius of curvature of the trajectory, the high-energy beam absorption chamber 54 being cooled, a movable type slit 55 for enabling selection of an analyzable range of energy, the movable type slit 55 being cooled, and a slit driver means 56 for adjusting the position of the slit 55.

The trajectory of the electron beam 51 is deflected within the vacuum chamber 52 by the uniform magnetic field generated from the deflection magnets not illustrated. Since this amount of deflection depends upon the electron energy, a most part of the low energy electrons enter into the low-energy beam absorption chamber 53 and are caught by and absorbed into the absorption chamber 53 while, on the other hand, a most part of the high energy electrons enter into the high-energy beam absorption chamber 54 and are caught by and absorbed into the absorption chamber 54.

The high-energy beam absorption chamber 54 is disposed on the outside of the vacuum chamber 52 and is cooled by passing of cooling water 64 therethrough. Since this chamber portion 54 is located outside the vacuum chamber 52, the passage of the cooling water 64 which is installable between the magnetic poles of the deflection magnets not illustrated can be selected. For this reason, this passage of the cooling water can be designed so as to obtain a sufficiently high level of cooling performance. Also, while the cooling water 65 is also caused to pass through the low-energy beam absorption chamber 53, since in the portion of the wall of the absorption chamber 53 having low energy electrons incident thereupon a flow passage 63 is narrowed by means of a flow adjusting part 57, the flow velocity of the cooling water 65 there becomes high. Since therefore it becomes possible to loosen the critical heat flow velocity requirement, ensuring the cooling performance there becomes possible. Also, since the narrowed flow passage 63 is only there, it is possible to minimize the pressure loss of the cooling water piping system.

Note that the energy of the electrons to be absorbed by the low-energy beam absorption chamber 53 and high-energy beam absorption chamber 54 is determined by the intensity of the magnetic field generated by the deflection magnets not illustrated, the configurations of these absorption chambers and the relative disposition between these chambers and the trajectory of the electron beam 51. Note also that the amount of electron caught by the absorption chambers is determined by the energy distribution of the electrons within the electron beam 51 having entered into the energy analyzer.

The electron beam 51 having not been caught by and absorbed into the both chambers 53 and 54, i.e., having an energy width narrowed to some extent arrives at a portion where the movable type slit 55 is installed. In this portion of installation, the energy width of the electron beam 51 is further adjusted, i.e., the energy width is further narrowed. That is to say, part 62 of the electron beam 51 is caught by and absorbed into the movable type slit 55 provided with an opening 55a in order to set a center energy. As a result of this, the electron beam 58 having passed through the slit 55 has a prescribed center energy and energy width.

As mentioned above, for the energy analyzing operation, two stages of operation are performed, one for performing catch and absorption of the electrons having an energy width outside a prescribed range by the low-energy beam absorption chamber 53 and high-energy beam absorption chamber 54, and the other for thereafter performing catch and absorption thereof by the movable type slit 55.

Since the width of opening of the movable type slit 55 corresponds to an energy width to be selected (the absolute value depends upon the intensity of the deflection field), in a case where a selected energy width is determined beforehand, the movable type slit 55 may be formed into an integral type slit (wherein a high-energy side slit and a low-energy side slit are integrated with each other and the positions thereof are simultaneously set). However, in a case where the selected energy width is arbitrarily set, it is necessary to enable independent setting of the respective positions of the high-energy side slit and low-energy side slit.

Note the following. When an electron beam enters into the low-energy beam absorption chamber 53, high-energy beam absorption chamber 54 and slit 55, each of these elements generates damping X rays. Also, when electrons having an energy larger than that corresponding to the atomic binding energy in the material of each element enter thereinto, neutrons are released. Therefore, for countermeasures against X rays, a low-atomic-number material needs to be used as the material of such element and, for countermeasures against neutrons, selection of a relevant material needs to be made with the binding energy taken into consideration.

As mentioned above, although concrete explanation has been given of a case where the energy analyzer of the present invention is an electron beam generator apparatus, the present invention is not limited to such an electron beam generator apparatus only. The invention can be also similarly applied to the energy analysis for ion beam such as hydrogen ion beam. Also, although regarding the magnetic field reference has been made to a uniform magnetic field, the invention can be also similarly applied to the energy analysis which uses a multi-pole type magnet based on the use of multiple magnetic poles.

What is claimed is:

1. A charged particle accelerator apparatus comprising an accelerating tube having a plurality of resonance cavities formed axially in its interior and having charged particles caused to pass therethrough from one end side thereof to the other end side thereof, an input coupler provided at one end portion of the accelerating tube for inputting an accelerating microwave, and a dummy load provided at the other end portion thereof through an output coupler, characterized by further comprising cooling means provided on the outside of the accelerating tube for making uniform thermal expansions of the respective resonance cavities with respect to a thermal load distribution decreasing from the one end side of the accelerating tube toward the other end side thereof and frequency adjusting means for adjusting the frequency of the accelerating microwave input through the input coupler to a resonance frequency of the respective resonance cavities having been subjected to uniform thermal expansion.

2. A charged particle accelerator apparatus comprising an accelerating tube having a plurality of resonance cavities formed axially in its interior and having charged particles caused to pass therethrough from one end side thereof to the other end side thereof, an input coupler provided at one end portion of the accelerating tube for inputting an accelerating microwave, and a dummy load provided at the other end portion thereof through an output coupler, characterized by further comprising cooling means provided on the outside of the accelerating tube for making uniform thermal expansions of the respective resonance cavities with respect to a thermal load distribution decreasing from the one end side of the accelerating tube toward the other end side thereof.

3. An electronic sterilizer apparatus comprising an electron gun for generating a charged particle beam, the charged particle accelerator apparatus of claim 1 for accelerating the charged particle beam, an energy analyzer for taking out only a beam component having a prescribed width of energy from the accelerated charged particle beam, and a scan horn for irradiating the charged particle beam from the energy analyzer onto a sterilization object while scanning it thereover.

4. An electronic sterilizer apparatus as set forth in claim 3, characterized by comprising the energy analyzer which is an analyzer adapted to cause the charged particle beam from the charged particle accelerator apparatus to enter into a vacuum chamber and cause deflection of this beam by use of a magnetic field to thereby analyze the energy thereof, the analyzer comprising a low-energy beam absorption chamber disposed at such a position as to surround a center of the radius of curvature of a trajectory of the deflected beam within the vacuum chamber constituting a path of this beam and as to stop forward travel of a low-energy beam contained therein, the low-energy beam absorption chamber being arranged to be cooled, a high-energy beam absorption chamber disposed at such a position as to oppose the center of the radius of curvature of the trajectory within the vacuum chamber and as to stop forward travel of a high-energy beam contained in the beam, the high-energy beam absorption chamber being arranged to be cooled, and a movable type slit whose opening width is adjusted on the trajectory of the deflected beam to thereby enable selection of an analyzable range of energy thereof, the movable type slit being arranged to be cooled.

5. An electronic sterilizer apparatus as set forth in claim 4, characterized by comprising the energy analyzer wherein the movable type slit is provided with a plurality of slits each of which can be independently driven and positionally set.

6. An electronic sterilizer apparatus comprising an electron gun for generating a charged particle beam, the charged particle accelerator apparatus of claim 2 for accelerating the charged particle beam, an energy analyzer for taking out only a beam component having a prescribed width of energy from the accelerated charged particle beam, and a scan horn for irradiating the charged particle beam from the energy analyzer onto a sterilization object while scanning it thereover.

* * * * *